United States Patent
Walz (10) Patent No.: US 8,875,701 B2
(45) Date of Patent: Nov. 4, 2014

(54) INHALER

(75) Inventor: Michael Walz, Bingen (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 1214 days.

(21) Appl. No.: 12/296,774

(22) PCT Filed: Apr. 4, 2007

(86) PCT No.: PCT/EP2007/053326
§ 371 (c)(1),
(2), (4) Date: Dec. 2, 2008

(87) PCT Pub. No.: WO2007/118801
PCT Pub. Date: Oct. 25, 2007

(65) Prior Publication Data
US 2009/0277446 A1  Nov. 12, 2009

(30) Foreign Application Priority Data

Apr. 11, 2006  (DE) .......................... 10 2006 016 904

(51) Int. Cl.
*A61M 15/00* (2006.01)
*A61M 11/00* (2006.01)

(52) U.S. Cl.
CPC ... *A61M 15/0028* (2013.01); *A61M 2205/6045* (2013.01); *A61M 11/003* (2014.02); *A61M 15/0035* (2014.02); *A61M 2205/583* (2013.01); *A61M 15/0021* (2014.02); *A61M 15/0026* (2014.02); *A61M 2202/064* (2013.01)
USPC .................................. 128/203.15; 128/203.21

(58) Field of Classification Search
USPC ................. 128/203.15, 203.21; 222/325–327, 222/83.5, 85
See application file for complete search history.

(56) References Cited

U.S. PATENT DOCUMENTS

| | | | |
|---|---|---|---|
| 2,146,202 A | | 2/1939 | Davenport et al. |
| 2,503,732 A | * | 4/1950 | Heisterkamp ............ 128/203.15 |
| 3,345,722 A | | 10/1967 | Stahlecker |
| 3,756,490 A | | 9/1973 | Zimmerman |
| 3,991,761 A | | 11/1976 | Cocozza |
| 4,318,455 A | | 3/1982 | Lapierre |
| 4,811,731 A | * | 3/1989 | Newell et al. ............ 128/203.15 |
| 4,891,165 A | | 1/1990 | Suthanthiran |
| 4,972,969 A | * | 11/1990 | Randklev .......................... 222/1 |

(Continued)

FOREIGN PATENT DOCUMENTS

| | | |
|---|---|---|
| CA | 2207219 A1 | 12/1998 |
| CA | 2448425 A1 | 12/2002 |

(Continued)

OTHER PUBLICATIONS

International Search Report for PCT/EP2007/053326 mailed Jul. 30, 2007.

(Continued)

*Primary Examiner* — Tan-Uyen T Ho
*Assistant Examiner* — Peter S Vasat
(74) *Attorney, Agent, or Firm* — Michael P. Morris; Mary-Ellen M. Devlin (57) ABSTRACT

Disclosed is an inhaler, especially a powder inhaler, for administering a medicament in the form of inhalable substances, substance formulations, or substance mixtures. Said inhaler comprises a housing that is provided with a chamber (4) for accommodating the substances. The chamber (4) is replaceably disposed inside the housing.

17 Claims, 2 Drawing Sheets

(56) References Cited

U.S. PATENT DOCUMENTS

| | | | |
|---|---|---|---|
| 4,995,385 A * | 2/1991 | Valentini et al. | 128/203.21 |
| 5,289,253 A | 2/1994 | Costello et al. | |
| 5,476,093 A | 12/1995 | Lankinen | |
| 5,497,944 A | 3/1996 | Weston et al. | |
| 5,577,497 A | 11/1996 | Mecikalski et al. | |
| 5,619,985 A | 4/1997 | Ohki et al. | |
| 5,673,686 A | 10/1997 | Villax et al. | |
| 5,685,294 A | 11/1997 | Gupte et al. | |
| 5,785,049 A | 7/1998 | Smith et al. | |
| 5,881,721 A | 3/1999 | Bunce et al. | |
| 5,947,118 A | 9/1999 | Hochrainer et al. | |
| 6,286,507 B1 | 9/2001 | Jahnsson | |
| 6,550,472 B2 * | 4/2003 | Litherland et al. | 128/200.18 |
| 6,557,549 B2 | 5/2003 | Schmidt et al. | |
| 6,810,872 B1 | 11/2004 | Ohki et al. | |
| 7,213,595 B2 | 5/2007 | Capon et al. | |
| 7,429,687 B2 | 9/2008 | Kauth et al. | |
| 7,559,326 B2 | 7/2009 | Smith et al. | |
| 7,905,229 B2 | 3/2011 | Giroux et al. | |
| 2004/0011356 A1 * | 1/2004 | Sullivan | 128/200.14 |
| 2004/0025871 A1 | 2/2004 | Davies | |
| 2004/0173211 A1 * | 9/2004 | Kladders et al. | 128/203.15 |
| 2004/0255940 A1 * | 12/2004 | Pera | 128/203.15 |
| 2008/0054099 A1 | 3/2008 | Giroux et al. | |
| 2008/0156330 A1 | 7/2008 | Smith et al. | |
| 2008/0197045 A1 | 8/2008 | Metzger et al. | |
| 2009/0137621 A1 | 5/2009 | Hochrainer et al. | |
| 2009/0277446 A1 | 11/2009 | Walz | |
| 2011/0036347 A1 | 2/2011 | Morgan, III et al. | |

FOREIGN PATENT DOCUMENTS

| | | |
|---|---|---|
| CA | 2 507 579 A1 | 6/2004 |
| CA | 2 513 130 A1 | 7/2004 |
| CA | 2616174 A1 | 2/2007 |
| DE | 10126924 A1 | 12/2002 |
| EP | 0666085 A1 | 8/1995 |
| EP | 0 696 458 A2 | 2/1996 |
| EP | 0869079 A2 | 10/1998 |
| JP | 2001510378 A | 7/2001 |
| WO | 9102558 A1 | 3/1991 |
| WO | 9406498 A1 | 3/1994 |
| WO | 9428958 A1 | 12/1994 |
| WO | 9701365 A1 | 1/1997 |
| WO | 9834661 A1 | 8/1998 |
| WO | 9945987 A1 | 9/1999 |
| WO | 0051672 A1 | 9/2000 |
| WO | 0064779 A1 | 11/2000 |
| WO | 0172605 A1 | 10/2001 |
| WO | 02/24268 A1 | 3/2002 |
| WO | 0247796 A2 | 6/2002 |
| WO | 02056948 A1 | 7/2002 |
| WO | 02/074374 A1 | 9/2002 |
| WO | 02072449 A1 | 9/2002 |
| WO | 2004/047796 A2 | 6/2004 |
| WO | 2004/062716 A1 | 7/2004 |
| WO | 2004067069 A2 | 8/2004 |
| WO | 2005091136 A1 | 9/2005 |
| WO | 2006028639 A1 | 3/2006 |
| WO | 2007012628 A2 | 2/2007 |
| WO | 2007118801 A1 | 10/2007 |
| WO | 2008028092 A2 | 3/2008 |
| WO | 2009011047 A1 | 1/2009 |

OTHER PUBLICATIONS

Bell et al., "Dry powder aerosols I: A new powder inhalation device". Journal of Pharmaeceutical Sciences, vol. 60, No. 10, Oct. 1971, pp. 1559-1564.

Cox et al., "Administration of Disodium Cromoglycate". British Medical Journal, vol. 2, Jun. 1969, p. 634.

* cited by examiner

INHALER

"This application is a national phase entry under 35 U.S.C. 271 of international application PCT/EP2007/053326, filed Apr. 4, 2007, which claims priority to German Application No. DE 10 2006 016 904.2, filed Apr. 11, 2006, each of which is hereby incorporated by reference in its entirety".

The invention relates to an inhaler, particularly a powder inhaler, for administering a medicament in the form of inhalable substances, formulations or mixtures of substances having a housing comprising a chamber for holding the substances.

EP 0 911 047 A1 discloses an inhaler for inhaling powdered medicaments from capsules, which comprises a lower part having two windows and a plate in which are provided capsule holders and air inlet openings. In addition, an inhalation chamber is connected to the plate, on which is provided a head having two sharp pins which is movable counter to a spring. A mouthpiece tube is connected to an upper part of the inhaler and a lid is foldably connected to the lower part, the plate and the upper part. It has proved problematic that the inhaler should be cleaned at least once a month in order to remove medicament residues, in particular, as these residues may lead to regulatory problems if they become detached at irregular intervals and are expelled together with the actual dose. For cleaning, the lid has to be opened and both the mouthpiece tube and the plate have to be pivoted away from the lower part. The complete inhaler is then rinsed out with preferably warm water and dried in the air. It is also necessary to clean the inhaler by wiping it with damp cotton wool or cotton wool buds. The cleaning process which is relatively easy to carry out is, however, performed with different degrees of thoroughness depending on the personal habits of the user of the inhaler, their age and level of health. Moreover, the cleaning described above is generally successful in the case of a medicament with a low content of active substance or a water-soluble active substance, whereas it is difficult to carry out in the case of a medicament with a high content of active substance or an active substance which has low solubility in water.

The aim of the invention is to provide an inhaler of the type mentioned hereinbefore which is easy for a patient to handle.

According to the invention the aim is achieved by having the chamber replaceably mounted in the housing.

As a result of this measure there is no need to use water to clean medicament residues from the inhaler and the risk of a caking of powder caused by inadequate drying of the inhaler is substantially reduced.

Inhalers are known under the brand names HandiHaler®, Spinhaler®, Rotahaler®, Aerolizer®, Flowcaps®, Turbospin®, AIR DPI®, Orbital®, Directhaler® and/or are described in DE 33 45 722, EP 0 591 136, DE 43 18 455, WO 91/02558, FR-A-2 146 202, U.S. Pat. No. 4,069,819, EP 666085, EP 869079, U.S. Pat. No. 3,991,761, WO 99/45987, WO 200051672, Bell, J. Pharm. Sci. 60, 1559 (1971); Cox, Brit. Med. J. 2, 634 (1969). Examples of powder inhalers include single- or multi-dose powder inhalers, particularly the Spinhaler®, Rotahaler®, Aerolizer®, Inhalator@, HandiHaler®, Diskhaler®, Diskus®, Accuhaler®, Aerohaler®, Eclipse®, Turbohaler®, Turbuhaler®, Easyhaler®, Novolizer®, Clickhaler®, Pulvinal®, Novolizer®, SkyeHaler®, Xcelovair®, Pulvina®, Taifun®, MAGhaler®, Twisthaler® and the Jethaler®.

According to one feature, the chamber is configured so as to accommodate a capsule containing the medicament. The capsule placed in the chamber thus forms the actual receptacle for the medicament.

The compounds listed below may be used in the device according to the invention on their own or in combination. In the compounds mentioned below, W is a pharmacologically active substance and is selected (for example) from among the betamimetics, anticholinergics, corticosteroids, PDE4-inhibitors, LTD4-antagonists, EGFR-inhibitors, dopamine agonists, H1-antihistamines, PAF-antagonists and PJ3-kinase inhibitors. Moreover, double or triple combinations of W may be combined and used in the device according to the invention. Combinations of W might be, for example:

W denotes a betamimetic, combined with an anticholinergic, corticosteroid, PDE4-inhibitor, EGFR-inhibitor or LTD4-antagonist, W denotes an anticholinergic, combined with a betamimetic, corticosteroid, PDE4-inhibitor, EGFR-inhibitor or LTD4-antagonist, W denotes a corticosteroid, combined with a PDE4-inhibitor, EGFR-inhibitor or LTD4-antagonist W denotes a PDE4-inhibitor, combined with an EGFR-inhibitor or LTD4-antagonist W denotes an EGFR-inhibitor, combined with an LTD4-antagonist.

The compounds used as betamimetics are preferably compounds selected from among albuterol, arformoterol, bambuterol, bitolterol, broxaterol, carbuterol, clenbuterol, fenoterol, formoterol, hexoprenaline, ibuterol, isoetharine, isoprenaline, levosalbutamol, mabuterol, meluadrine, metaproterenol, orciprenaline, pirbuterol, procaterol, reproterol, rimiterol, ritodrine, salmefamol, salmeterol, soterenol, sulphonterol, terbutaline, tiaramide, tolubuterol, zinterol, CHF-1035, HOKU-81, KUL-1248 and 3-(4-{6-[2-hydroxy-2-(4-hydroxy-3-hydroxymethyl-phenyl)-ethylamino]-hexyloxy}-butyl)-benzyl-sulphonamide 5-[2-(5,6-diethyl-indan-2-ylamino)-1-hydroxy-ethyl]-8-hydroxy-1H-quinolin-2-one 4-hydroxy-7-[2-{[2-{[3-(2-phenylethoxy)propyl] sulphonyl}ethyl]-amino}ethyl]-2(3H)-benzothiazolone 1-(2-fluoro-4-hydroxyphenyl)-2-[4-(1-benzimidazolyl)-2-methyl-2-butylamino]ethanol 1-[3-(4-methoxybenzyl-amino)-4-hydroxyphenyl]-2-[4-(1-benzimidazolyl)-2-methyl-2-butylamino]ethanol 1-[2H-5-hydroxy-3-oxo-4H-1,4-benzoxazin-8-yl]-2-[3-(4-N,N-dimethylaminophenyl)-2-methyl-2-propylamino] ethanol 1-[2H-5-hydroxy-3-oxo-4H-1,4-benzoxazin-8-yl]-2-[3-(4-methoxyphenyl)-2-methyl-2-propylamino]ethanol 1-[2H-5-hydroxy-3-oxo-4H-1,4-benzoxazin-8-yl]-2-[3-(4-n-butyloxyphenyl)-2-methyl-2-propylamino]ethanol 1-[2H-5-hydroxy-3-oxo-4H-1,4-benzoxazin-8-yl]-2-{4-[3-(4-methoxyphenyl)-1,2,4-triazol-3-yl]-2-methyl-2-butylamino}ethanol 5-hydroxy-8-(1-hydroxy-2-isopropylaminobutyl)-2H-1,4-benzoxazin-3-(4H)-one 1-(4-amino-3-chloro-5-trifluoromethylphenyl)-2-tert.-butylamino)ethanol 6-hydroxy-8-{1-hydroxy-2-[2-(4-methoxy-phenyl)-1,1-dimethyl-ethylamino]-ethyl}-4H-benzo[1,4]oxazin-3-one 6-hydroxy-8-{1-hydroxy-2-[2-(ethyl 4-phenoxy-acetate)-1,1-dimethyl-ethylamino]-ethyl}-4H-benzo[1,4]oxazin-3-one 6-hydroxy-8-{1-hydroxy-2-[2-(4-phenoxy-acetic acid)-1,1-dimethyl-ethylamino]-ethyl}-4H-benzo[1,4]oxazin-3-one 8-{2-[1,1-dimethyl-2-(2,4,6-trimethylphenyl)-ethylamino]-1-hydroxy-ethyl}-6-hydroxy-4H-benzo[1,4]oxazin-3-one 6-hydroxy-8-{1-hydroxy-2-[2-(4-hydroxy-phenyl)-1,1-dimethyl-ethylamino]-ethyl}-4H-benzo[1,4]oxazin-3-one 6-hydroxy-8-{1-hydroxy-2-[2-(4-isopropyl-phenyl)-1.1 dimethyl-ethylamino]-ethyl}-4H-benzo[1,4]oxazin-3-one 8-{2-[2-(4-ethyl-phenyl)-1,1-dimethyl-ethylamino]-1-hydroxy-ethyl}-6-hydroxy-4H-benzo[1,4]oxazin-3-one 8-{2-[2-(4-ethoxy-phenyl)-1,1-dimethyl-ethylamino]-1-hydroxy-ethyl}-6-hydroxy-4H-benzo[1,4]oxazin-3-one 4-(4-{2-[2-hydroxy-2-(6-hydroxy-3-oxo-3,4-dihydro-2H-benzo[1,4]oxazin-8-yl)-ethylamino]-2-methyl-propyl}-phenoxy)-butyric acid 8-{2-[2-(3.4-difluoro-phenyl)-1,1-dimethyl-ethylamino]-1-hydroxy-ethyl}-6-hydroxy-4H-benzo[1,4]oxazin-3-one 1-(4-ethoxy-carbonylamino-3-cyano-5-fluorophenyl)-2-(tert-butylamino)ethanol 2-hydroxy-5-(1-hydroxy-2-{2-[4-(2-hydroxy-2-phenyl-ethylamino)-phenyl]-ethylamino}-ethyl)-benzaldehyde N-[2-hydroxy-5-(1-hydroxy-2-{2-[4-(2-hydroxy-2-phenyl-ethylamino)-phenyl]-ethylamino}-ethyl)-phenyl]-formamide 8-hydroxy-5-(1-hydroxy-2-{2-[4-(6-methoxy-biphenyl-3-ylamino)-phenyl]-ethylamino}-ethyl)-1H-quinolin-2-one 8-hydroxy-5-[1-hydroxy-2-(6-phenethylamino-hexylamino)-ethyl]-1H-quinolin-2-one 5-[2-(2-{4-[4-(2-amino-2-methyl-propoxy)-phenylamino]-phenyl}-ethylamino)-1-hydroxy-ethyl]-8-hydroxy-1H-quinolin-2-one

[3-(4-{6-[2-hydroxy-2-(4-hydroxy-3-hydroxymethyl-phenyl)-ethylamino]-hexyloxy}-butyl)-5-methyl-phenyl]-urea 4-(2-{6-[2-(2,6-dichloro-benzyloxy)-ethoxy]-hexylamino}-1-hydroxy-ethyl)-2-hydroxymethyl-phenol 3-(4-{6-[2-hydroxy-2-(4-hydroxy-3-hydroxymethyl-phenyl)-ethylamino]-hexyloxy}-butyl)-benzylsulphonamide 3-(3-{7-[2-hydroxy-2-(4-hydroxy-3-hydroxymethyl-phenyl)-ethylamino]-heptyloxy}-propyl)-benzylsulphonamide

4-(2-{6-[4-(3-cyclopentanesulphonyl-phenyl)-butoxy]-hexylamino}-1-hydroxy-ethyl)-2-hydroxymethyl-phenol N-Adamantan-2-yl-2-(3-{2-[2-hydroxy-2-(4-hydroxy-3-hydroxymethyl-phenyl)-ethylamino]-propyl}-phenyl)-acetamide optionally in the form of the racemates, enantiomers, diastereomers thereof and optionally in the form of the pharmacologically acceptable acid addition salts, solvates or hydrates thereof. According to the invention the acid addition salts of the betamimetics are preferably selected from among the hydrochloride, hydrobromide, hydriodide, hydrosulphate, hydrophosphate, hydromethanesulphonate, hydronitrate, hydromaleate, hydroacetate, hydrocitrate, hydrofumarate, hydrotartrate, hydroxalate, hydrosuccinate, hydrobenzoate and hydro-p-toluenesulphonate.

The anticholinergics used are preferably compounds selected from among the tiotropium salts, preferably the bromide salt, oxitropium salts, preferably the bromide salt, flutropium salts, preferably the bromide salt, ipratropium salts, preferably the bromide salt, glycopyrronium salts, preferably the bromide salt, trospium salts, preferably the chloride salt, tolterodine. In the above-mentioned salts the cations are the pharmacologically active constituents. As anions the above-mentioned salts may preferably contain the chloride, bromide, iodide, sulphate, phosphate, methanesulphonate, nitrate, maleate, acetate, citrate, fumarate, tartrate, oxalate, succinate, benzoate or p-toluenesulphonate, while chloride, bromide, iodide, sulphate, methanesulphonate or p-toluenesulphonate are preferred as counterions. Of all the salts the chlorides, bromides, iodides and methanesulphonates are particularly preferred.

Other preferred anticholinergics are selected from among the salts of formula AC-1 wherein $X^-$ denotes an anion with a single negative charge, preferably an anion selected from among the fluoride, chloride, bromide, iodide, sulphate, phosphate, methanesulphonate, nitrate, maleate, acetate, citrate, fumarate, tartrate, oxalate, succinate, benzoate and p-toluenesulphonate, preferably an anion with a single negative charge, particularly preferably an anion selected from among the fluoride, chloride, bromide, methanesulphonate and p-toluenesulphonate, particularly preferably bromide, optionally in the form of the racemates, enantiomers or hydrates thereof. Of particular importance are those pharmaceutical combinations which contain the enantiomers of formula AC-1-en wherein $X^-$ may have the above-mentioned meanings. Other preferred anticholinergics are selected from the salts of formula AC-2 wherein R denotes either methyl or ethyl and wherein $X^-$ may have the above-mentioned meanings. In an alternative embodiment the compound of formula AC-2 may also be present in the form of the free base AC-2-base.

AC-2-base

Other specified compounds are:
tropenol 2,2-diphenylpropionate methobromide,
scopine 2,2-diphenylpropionate methobromide,
scopine 2-fluoro-2,2-diphenylacetate methobromide,
tropenol 2-fluoro-2,2-diphenylacetate methobromide;
tropenol 3,3',4,4'-tetrafluorobenzilate methobromide,
scopine 3,3',4,4'-tetrafluorobenzilate methobromide,
tropenol 4,4'-difluorobenzilate methobromide,
scopine 4,4'-difluorobenzilate methobromide,
tropenol 3,3'-difluorobenzilate methobromide,
scopine 3,3'-difluorobenzilate methobromide;
tropenol 9-hydroxy-fluorene-9-carboxylate methobromide;
tropenol 9-fluoro-fluorene-9-carboxylate methobromide;
scopine 9-hydroxy-fluorene-9-carboxylate methobromide;
scopine 9-fluoro-fluorene-9-carboxylate methobromide;
tropenol 9-methyl-fluorene-9-carboxylate methobromide;
scopine 9-methyl-fluorene-9-carboxylate methobromide;
cyclopropyltropine benzilate methobromide;
cyclopropyltropine 2,2-diphenylpropionate methobromide;
cyclopropyltropine 9-hydroxy-xanthene-9-carboxylate methobromide;
cyclopropyltropine 9-methyl-fluorene-9-carboxylate methobromide;
cyclopropyltropine 9-methyl-xanthene-9-carboxylate methobromide;
cyclopropyltropine 9-hydroxy-fluorene-9-carboxylate methobromide;
cyclopropyltropine methyl 4,4'-difluorobenzilate methobromide.
tropenol 9-hydroxy-xanthene-9-carboxylate methobromide;
scopine 9-hydroxy-xanthene-9-carboxylate methobromide;
tropenol 9-methyl-xanthene-9-carboxylate methobromide;
scopine 9-methyl-xanthene-9-carboxylate methobromide;
tropenol 9-ethyl-xanthene-9-carboxylate methobromide;
tropenol 9-difluoromethyl-xanthene-9-carboxylate methobromide;
scopine 9-hydroxymethyl-xanthene-9-carboxylate methobromide, The above-mentioned compounds may also be used as salts within the scope of the present invention, wherein instead of the methobromide the salts metho-X are used, wherein X may have the meanings given hereinbefore for $X^-$.

As corticosteroids it is preferable to use compounds selected from among beclomethasone, betamethasone, budesonide, butixocort, ciclesonide, deflazacort, dexamethasone, etiprednol, flunisolide, fluticasone, loteprednol, mometasone, prednisolone, prednisone, rofleponide, triamcinolone, RPR-106541, NS-126, ST-26 and (S)-fluoromethyl 6,9-difluoro-17-[(2-furanylcarbonyl)oxy]-11-hydroxy-16-methyl-3-oxo-androsta-1,4-diene-17-carbothionate (S)-(2-oxo-tetrahydro-furan-3 S-yl)6,9-difluoro-11-hydroxy-16-methyl-3-oxo-17-propionyloxy-androsta-1,4-diene-17-carbothionate, cyanomethyl 6α,9α-difluoro-11β-hydroxy-16α-methyl-3-oxo-17α-(2,2,3,3-tertamethylcyclopropylcarbonyl)oxy-androsta-1,4-diene-17β-carboxylate optionally in the form of the racemates, enantiomers or diastereomers thereof and optionally in the form of the salts and derivatives thereof, the solvates and/or hydrates thereof. Any reference to steroids includes a reference to any salts or derivatives, hydrates or solvates thereof which may exist. Examples of possible salts and derivatives of the steroids may be: alkali metal salts, such as for example sodium or potassium salts, sulphobenzoates, phosphates, isonicotinates, acetates, dichloroacetates, propionates, dihydrogen phosphates, palmitates, pivalates or furoates.

PDE4-inhibitors which may be used are preferably compounds selected from among enprofyllin, theophyllin, roflumilast, ariflo (cilomilast), tofimilast, pumafentrin, lirimilast, arofyllin, atizoram, D-4418, Bay-198004, BY343, CP-325.366, D-4396 (Sch-351591), AWD-12-281 (GW-842470), NCS-613, CDP-840, D-4418, PD-168787, T-440, T-2585, V-11294A, Cl-1018, CDC-801, CDC-3052, D-22888, YM-58997, Z-15370 and N-(3,5-dichloro-1-oxo-pyridin-4-yl)-4-difluoromethoxy-3-cyclopropylmethoxybenzamide (−)p-[(4aR*,10bS*)-9-ethoxy-1,2,3,4,4a,10b-hexahydro-8-methoxy-2-methylbenzo[s][1,6]naphthyridin-6-yl]-N,N-diisopropylbenzamide (R)-(+)-1-(4-bromobenzyl)-4-[(3-cyclopentyloxy)-4-methoxyphenyl]-2-pyrrolidone 3-(cyclopentyloxy-4-methoxyphenyl)-1-(4-N'-[N-2-cyano-5-methyl-isothioureido]benzyl)-2-pyrrolidone cis[4-cyano-4-(3-cyclopentyloxy-4-methoxyphenyl)cyclohexane-1-carboxylic acid]

2-carbomethoxy-4-cyano-4-(3-cyclopropylmethoxy-4-difluoromethoxy-phenyl)cyclohexan-1-one cis[4-cyano-4-(3-cyclopropylmethoxy-4-difluoromethoxyphenyl)cyclohexan-1-ol]

(R)-(+)-ethyl[4-(3-cyclopentyloxy-4-methoxyphenyl)pyrrolidin-2-ylidene]acetate (S)-(−)-ethyl[4-(3-cyclopentyloxy-4-methoxyphenyl)pyrrolidin-2-ylidene]acetate 9-cyclopentyl-5,6-dihydro-7-ethyl-3-(2-thienyl)-9H-pyrazolo[3,4-c]-1,2,4-triazolo[4,3-a]pyridine 9-cyclopentyl-5,6-dihydro-7-ethyl-3-(tert-butyl)-9H-pyrazolo[3,4-c]-1,2,4-triazolo[4,3-a]pyridine optionally in the form of the racemates, enantiomers or diastereomers thereof and optionally in the form of the pharmacologically acceptable acid addition salts thereof, the solvates and/or hydrates thereof. According to the invention the acid addition salts of the PDE4 inhibitors are preferably selected from among the hydrochloride, hydrobromide, hydriodide, hydrosulphate, hydrophosphate, hydromethanesulphonate, hydronitrate, hydromaleate, hydroacetate, hydrocitrate, hydrofumarate, hydrotartrate, hydroxalate, hydrosuccinate, hydrobenzoate and hydro-p-toluenesulphonate.

The LTD4-antagonists used are preferably compounds selected from among montelukast, pranlukast, zafirlukast, MCC-847 (ZD-3523), MN-001, MEN-91507 (LM-1507), VUF-5078, VUF-K-8707, L-733321 and 1-(((R)-(3-(2-(6,7-difluoro-2-quinolinyl)ethenyl)phenyl)-3-(2-(2-hydroxy-2-propyl)phenyl)thio)methylcyclopropane-acetic acid, 1-(((1(R)-3 (3-(2-(2,3-dichlorothieno[3,2-b]pyridin-5-yl)-(E)-ethenyl)phenyl)-3-(2-(1-hydroxy-1-methylethyl)phenyl)propyl)thio)methyl)cyclopropaneacetic acid

[2-[[2-(4-tert-butyl-2-thiazolyl)-5-benzofuranyl]oxymethyl]phenyl]acetic acid optionally in the form of the racemates, enantiomers or diastereomers thereof and optionally in the form of the pharmacologically acceptable acid addition salts, solvates and/or hydrates thereof. According to the invention these acid addition salts are preferably selected from among the hydrochloride, hydrobromide, hydroiodide, hydrosulphate, hydrophosphate, hydromethanesulphonate, hydronitrate, hydromaleate, hydroacetate, hydrocitrate, hydrofumarate, hydrotartrate, hydroxalate, hydrosuccinate, hydrobenzoate and hydro-p-toluenesulphonate. By salts or derivatives which the LTD4-antagonists may optionally be capable of forming are meant, for example: alkali metal salts, such as for example sodium or potassium salts, alkaline earth metal salts, sulphobenzoates, phosphates, isonicotinates, acetates, propionates, dihydrogen phosphates, palmitates, pivalates or furoates.

EGFR-inhibitors which may be used are preferably compounds selected from among cetuximab, trastuzumab, ABX-EGF, Mab ICR-62 and 4-[(3-chloro-4-fluorophenyl)amino]-6-{[4-(morpholin-4-yl)-1-oxo-2-buten-1-yl]-amino}-7-cyclopropylmethoxy-quinazoline 4-[(3-chloro-4-fluorophenyl)amino]-6-{[4-(N,N-diethylamino)-1-oxo-2-buten-1-yl]-amino}-7-cyclopropylmethoxy-quinazoline 4-[(3-chloro-4-fluorophenyl)amino]-6-{[4-(N,N-dimethylamino)-1-oxo-2-buten-1-yl]amino}-7-cyclopropylmethoxy-quinazoline 4-[(R)-(1-phenyl-ethyl)amino]-6-{[4-(morpholin-4-yl)-1-oxo-2-buten-1-yl]amino}-7-cyclopentyloxy-quinazoline 4-[(3-chloro-4-fluoro-phenyl)amino]-6-{[4-((R)-6-methyl-2-oxo-morpholin-4-yl)-1-oxo-2-buten-1-yl]amino}-7-cyclopropylmethoxy-quinazoline 4-[(3-chloro-4-fluoro-phenyl)amino]-6-{[4-((R)-6-methyl-2-oxo-morpholin-4-yl)-1-oxo-2-buten-1-yl]amino}-7-[(S)-(tetrahydrofuran-3-yl)oxy]-quinazoline 4-[(3-chloro-4-fluoro-phenyl)amino]-6-{[4-((R)-2-methoxymethyl-6-oxo-morpholin-4-yl)-1-oxo-2-buten-1-yl]amino}-7-cyclopropylmethoxy-quinazoline 4-[(3-chloro-4-fluoro-phenyl)amino]-6-[2-((S)-6-methyl-2-oxo-morpholin-4-yl)-ethoxy]-7-methoxy-quinazoline 4-[(3-chloro-4-fluorophenyl)amino]-6-({4-[N-(2-methoxy-ethyl)-N-methyl-amino]-1-oxo-2-buten-1-yl}amino)-7-cyclopropylmethoxy-quinazoline 4-[(3-chloro-4-fluorophenyl)amino]-6-{[4-(N,N-dimethylamino)-1-oxo-2-buten-1-yl]amino}-7-cyclopentyloxy-quinazoline 4-[(R)-(1-phenyl-ethyl)amino]-6-{[4-(N,N-to-(2-methoxy-ethyl)-amino)-1-oxo-2-buten-1-yl]amino}-7-cyclopropylmethoxy-quinazoline 4-[(R)-(1-phenyl-ethyl)amino]-6-({4-[N-(2-methoxy-ethyl)-N-ethyl-amino]-1-oxo-2-buten-1-yl}amino)-7-cyclopropylmethoxy-quinazoline 4-[(R)-(1-phenyl-ethyl)amino]-6-({4-[N-(2-methoxy-ethyl)-N-methyl-amino]-1-oxo-2-buten-1-yl}amino)-7-cyclopropylmethoxy-quinazoline 4-[(R)-(1-phenyl-ethyl)amino]-6-({4-[N-(tetrahydropyran-4-yl)-N-methyl-amino]-1-oxo-2-buten-1-yl}amino)-7-cyclopropylmethoxy-quinazoline 4-[(3-chloro-4-fluorophenyl)amino]-6-{[4-(N,N-dimethylamino)-1-oxo-2-buten-1-yl]amino}-7-((R)-tetrahydrofuran-3-yloxy)-quinazoline 4-[(3-chloro-4-fluorophenyl)amino]-6-{[4-(N,N-dimethylamino)-1-oxo-2-buten-1-yl]amino}-7-((S)-tetrahydrofuran-3-yloxy)-quinazoline 4-[(3-chloro-4-fluorophenyl)amino]-6-({4-[N-(2-methoxy-ethyl)-N-methyl-amino]-1-oxo-2-buten-1-yl}amino)-7-cyclopentyloxy-quinazoline 4-[(3-chloro-4-fluorophenyl)amino]-6-{[4-(N-cyclopropyl-N-methyl-amino)-1-oxo-2-buten-1-yl]amino}-7-cyclopentyloxy-quinazoline 4-[(3-chloro-4-fluorophenyl)amino]-6-{[4-(N,N-dimethylamino)-1-oxo-2-buten-1-yl]amino}-7-[(R)-(tetrahydrofuran-2-yl)methoxy]-quinazoline 4-[(3-chloro-4-fluorophenyl)amino]-6-{[4-(N,N-dimethylamino)-1-oxo-2-buten-1-yl]amino}-7-[(S)-(tetrahydrofuran-2-yl)methoxy]-quinazoline 4-[(3-ethynyl-phenyl)amino]-6.7-to-(2-methoxy-ethoxy)-quinazoline 4-[(3-chloro-4-fluorophenyl)amino]-7-[3-(morpholin-4-yl)-propyloxy]-6-[(vinyl-carbonyl)amino]-quinazoline 4-[(R)-(1-phenyl-ethyl)amino]-6-(4-hydroxy-phenyl)-7H-pyrrolo[2,3-d]pyrimidine 3-cyano-4-[(3-chloro-4-fluorophenyl)amino]-6-{[4-(N,N-dimethylamino)-1-oxo-2-buten-1-yl]amino}-7-ethoxy-quinoline 4-{[3-chloro-4-(3-fluoro-benzyloxy)-phenyl]amino}-6-(5-{[(2-methanesulphonyl-ethyl)amino]methyl}-furan-2-yl)quinazoline 4-[(R)-(1-phenyl-ethyl)amino]-6-{[4-((R)-6-methyl-2-oxomorpholin-4-yl)-1-oxo-2-buten-1-yl]amino}-7-methoxyquinazoline 4-[(3-chloro-4-fluorophenyl)amino]-6-{[4-(morpholin-4-yl)-1-oxo-2-buten-1-yl]-amino}-7-[(tetrahydrofuran-2-yl)methoxy]-quinazoline 4-[(3-chloro-4-fluorophenyl)amino]-6-({4-[N,N-to-(2-methoxy-ethyl)-amino]-1-oxo-2-buten-1-yl}amino)-7-[(tetrahydrofuran-2-yl)methoxy]-quinazoline 4-[(3-ethynyl-phenyl)amino]-6-{[4-(5.5-dimethyl-2-oxo-morpholin-4-yl)-1-oxo-2-buten-1-yl]amino}-quinazoline 4-[(3-chloro-4-fluoro-phenyl)amino]-6-[2-(2,2-dimethyl-6-oxo-morpholin-4-yl)-ethoxy]-7-methoxy-quinazoline 4-[(3-chloro-4-fluoro-phenyl)amino]-6-[2-(2,2-dimethyl-6-oxo-morpholin-4-yl)-ethoxy]-7-[(R)-(tetrahydrofuran-2-yl)methoxy]-quinazoline 4-[(3-chloro-4-fluoro-phenyl)amino]-7-[2-(2,2-dimethyl-6-oxo-morpholin-4-yl)-ethoxy]-6-[(S)-(tetrahydrofuran-2-yl)methoxy]-quinazoline 4-[(3-chloro-4-fluoro-phenyl)amino]-6-{2-[4-(2-oxo-morpholin-4-yl)-piperidin-1-yl]-ethoxy}-7-methoxy-quinazoline 4-[(3-chloro-4-fluoro-phenyl)amino]-6-[1-(tert.-butyloxycarbonyl)-piperidin-4-yloxy]-7-methoxy-quinazoline 4-[(3-chloro-4-fluoro-phenyl)amino]-6-(trans-4-amino-cyclohexan-1-yloxy)-7-methoxy-quinazoline 4-[(3-chloro-4-fluoro-phenyl)amino]-6-(trans-4-methanesulphonylamino-cyclohexan-1-yloxy)-7-methoxy-quinazoline 4-[(3-chloro-4-fluoro-phenyl)amino]-6-(tetrahydropyran-3-yloxy)-7-methoxy-quinazoline 4-[(3-chloro-4-fluoro-phenyl)amino]-6-(1-methyl-piperidin-4-yloxy)-7-methoxy-quinazoline 4-[(3-chloro-4-fluoro-phenyl)amino]-6-{1-[(morpholin-4-yl)carbonyl]-piperidin-4-yl-oxy}-7-methoxy-quinazoline 4-[(3-chloro-4-fluoro-phenyl)amino]-6-{1-[(methoxymethyl)carbonyl]-piperidin-4-yl-oxy}-7-methoxy-quinazoline 4-[(3-chloro-4-fluoro-phenyl)amino]-6-(piperidin-3-yloxy)-7-methoxy-quinazoline 4-[(3-chloro-4-fluoro-phenyl)amino]-6-[1-(2-acetylaminoethyl)-piperidin-4-yloxy]-7-methoxy-quinazoline 4-[(3-chloro-4-fluoro-phenyl)amino]-6-(tetrahydropyran-4-yloxy)-7-ethoxy-quinazoline 4-[(3-chloro-4-fluoro-phenyl)amino]-6-((S)-tetrahydrofuran-3-yloxy)-7-hydroxy-quinazoline 4-[(3-chloro-4-fluoro-phenyl)amino]-6-(tetrahydropyran-4-yloxy)-7-(2-methoxy-ethoxy)-quinazoline 4-[(3-chloro-4-fluoro-phenyl)amino]-6-{trans-4-[(dimethylamino)sulphonylamino]-cyclohexan-1-yloxy}-7-methoxy-quinazoline 4-[(3-chloro-4-fluoro-phenyl)amino]-6-{trans-4-[(morpholin-4-yl)carbonylamino]-cyclohexan-1-yloxy}-7-methoxy-quinazoline 4-[(3-chloro-4-fluoro-phenyl)amino]-6-{trans-4-[(morpholin-4-yl)sulphonylamino]-cyclohexan-1-yloxy}-7-methoxy-quinazoline 4-[(3-chloro-4-fluoro-phenyl)amino]-6-(tetrahydropyran-4-yloxy)-7-(2-acetylamino-ethoxy)-quinazoline 4-[(3-chloro-4-fluoro-phenyl)amino]-6-(tetrahydropyran-4-yloxy)-7-(2-methanesulphonylamino-ethoxy)-quinazoline 4-[(3-chloro-4-fluoro-phenyl)amino]-6-{1-[(piperidin-1-yl)carbonyl]-piperidin-4-yloxy}-7-methoxy-quinazoline 4-[(3-chloro-4-fluoro-phenyl)amino]-6-(1-aminocarbonylmethyl-piperidin-4-yloxy)-7-methoxy-quinazoline 4-[(3-chloro-4-fluoro-phenyl)amino]-6-(cis-4-{N—[(tetrahydropyran-4-yl)carbonyl]-N-methyl-amino}-cyclohexan-1-yloxy)-7-methoxy-quinazoline 4-[(3-chloro-4-fluoro-phenyl)amino]-6-(cis-4-{N—[(morpholin-4-yl)carbonyl]-N-methyl-amino}-cyclohexan-1-yloxy)-7-methoxy-quinazoline 4-[(3-chloro-4-fluoro-phenyl)amino]-6-(cis-4-{N—[(morpholin-4-yl)sulphonyl]-N-methyl-amino}-cyclohexan-1-yloxy)-7-methoxy-quinazoline 4-[(3-chloro-4-fluoro-phenyl)amino]-6-(trans-4-ethanesulphonylamino-cyclohexan-1-yloxy)-7-methoxy-quinazoline 4-[(3-chloro-4-fluoro-phenyl)amino]-6-(1-methanesulphonyl-piperidin-4-yloxy)-7-ethoxy-quinazoline 4-[(3-chloro-4-fluoro-phenyl)amino]-6-(1-methanesulphonyl-piperidin-4-yloxy)-7-(2-methoxy-ethoxy)-quinazoline 4-[(3-chloro-4-fluoro-phenyl)amino]-6-[1-(2-methoxy-acetyl)-piperidin-4-yloxy]-7-(2-methoxy-ethoxy)-quinazoline 4-[(3-chloro-4-fluoro-phenyl)amino]-6-(cis-4-acetylamino-cyclohexan-1-yloxy)-7-methoxy-quinazoline 4-[(3-ethynyl-phenyl)amino]-6-[1-(tert.-butyloxycarbonyl)-piperidin-4-yloxy]-7-methoxy-quinazoline 4-[(3-ethynyl-phenyl)amino]-6-(tetrahydropyran-4-yloxy]-7-methoxy-quinazoline 4-[(3-chloro-4-fluoro-phenyl)amino]-6-(cis-4-{N-[(piperidin-1-yl)carbonyl]-N-methyl-amino}-cyclohexan-1-yloxy)-7-methoxy-quinazoline 4-[(3-chloro-4-fluoro-phenyl)amino]-6-(cis-4-{N-[(4-methyl-piperazin-1-yl)carbonyl]-N-methyl-amino}-cyclohexan-1-yloxy)-7-methoxy-quinazoline 4-[(3-chloro-4-fluoro-phenyl)amino]-6-{cis-4-[(morpholin-4-yl)carbonylamino]-cyclohexan-1-yloxy}-7-methoxy-quinazoline 4-[(3-chloro-4-fluoro-phenyl)amino]-6-{1-[2-(2-oxopyrrolidin-1-yl)ethyl]-piperidin-4-yloxy}-7-methoxy-quinazoline 4-[(3-chloro-4-fluoro-phenyl)amino]-6-{1-[(morpholin-4-yl)carbonyl]-piperidin-4-yloxy}-7-(2-methoxy-ethoxy)-quinazoline 4-[(3-ethynyl-phenyl)amino]-6-(1-acetyl-piperidin-4-yloxy)-7-methoxy-quinazoline 4-[(3-ethynyl-phenyl)amino]-6-(1-methyl-piperidin-4-yloxy)-7-methoxy-quinazoline 4-[(3-ethynyl-phenyl)amino]-6-(1-methanesulphonyl-piperidin-4-yloxy)-7-methoxy-quinazoline 4-[(3-chloro-4-fluoro-phenyl)amino]-6-(1-methyl-piperidin-4-yloxy)-7(2-methoxy-ethoxy)-quinazoline 4-[(3-chloro-4-fluoro-phenyl)amino]-6-(1-isopropyloxycarbonyl-piperidin-4-yloxy)-7-methoxy-quinazoline 4-[(3-chloro-4-fluoro-phenyl)amino]-6-(cis-4-methylamino-cyclohexan-1-yloxy)-7-methoxy-quinazoline 4-[(3-chloro-4-fluoro-phenyl)amino]-6-{cis-4-[N-(2-methoxy-acetyl)-N-methyl-amino]-cyclohexan-1-yloxy}-7-methoxy-quinazoline 4-[(3-ethynyl-phenyl)amino]-6-(piperidin-4-yloxy)-7-methoxy-quinazoline 4-[(3-ethynyl-phenyl)amino]-6-[1-(2-methoxy-acetyl)-piperidin-4-yloxy]-7-methoxy-quinazoline 4-[(3-ethynyl-phenyl)amino]-6-{1-[(morpholin-4-yl)carbonyl]-piperidin-4-yloxy}-7-methoxy-quinazoline 4-[(3-chloro-4-fluoro-phenyl)amino]-6-{1-[(cis-2,6-dimethyl-morpholin-4-yl)carbonyl]-piperidin-4-yloxy}-7-methoxy-quinazoline 4-[(3-chloro-4-fluoro-phenyl)amino]-6-{1-[(2-methyl-morpholin-4-yl)carbonyl]-piperidin-4-yloxy}-7-methoxy-quinazoline 4-[(3-chloro-4-fluoro-phenyl)amino]-6-{1-[(S,S)-(2-oxa-5-aza-bicyclo[2,2,1]hept-5-yl)carbonyl]-piperidin-4-yloxy}-7-methoxy-quinazoline 4-[(3-chloro-4-fluoro-phenyl)amino]-6-{1-[(N-methyl-N-2-methoxyethyl-amino)carbonyl]-piperidin-4-yloxy}-7-methoxy-quinazoline 4-[(3-chloro-4-fluoro-phenyl)amino]-6-(1-ethyl-piperidin-4-yloxy)-7-methoxy-quinazoline 4-[(3-chloro-4-fluoro-phenyl)amino]-6-{1-[(2-methoxyethyl)carbonyl]-piperidin-4-yloxy}-7-methoxy-quinazoline 4-[(3-chloro-4-fluoro-phenyl)amino]-6-{1-[(3-methoxypropyl-amino)-carbonyl]-piperidin-4-yloxy}-7-methoxy-quinazoline 4-[(3-chloro-4-fluoro-phenyl)amino]-6-[cis-4-(N-methanesulphonyl-N-methyl-amino)-cyclohexan-1-yloxy]-7-methoxy-quinazoline 4-[(3-chloro-4-fluoro-phenyl)amino]-6-[cis-4-(N-acetyl-N-methyl-amino)-cyclohexan-1-yloxy]-7-methoxy-quinazoline 4-[(3-chloro-4-fluoro-phenyl)amino]-6-(trans-4-methylamino-cyclohexan-1-yloxy)-7-methoxy-quinazoline 4-[(3-chloro-4-fluoro-phenyl)amino]-6-[trans-4-(N-methanesulphonyl-N-methyl-amino)-cyclohexan-1-yloxy]-7-methoxy-quinazoline 4-[(3-chloro-4-fluoro-phenyl)amino]-6-(trans-4-dimethylamino-cyclohexan-1-yloxy)-7-methoxy-quinazoline 4-[(3-chloro-4-fluoro-phenyl)amino]-6-(trans-4-{N—[(morpholin-4-yl)carbonyl]-N-methyl-amino}-cyclohexan-1-yloxy)-7-methoxy-quinazoline 4-[(3-chloro-4-fluoro-phenyl)amino]-6-[2-(2,2-dimethyl-6-oxo-morpholin-4-yl)-ethoxy]-7-[(S)-(tetrahydrofuran-2-yl)methoxy]-quinazoline 4-[(3-chloro-4-fluoro-phenyl)amino]-6-(1-methanesulphonyl-piperidin-4-yloxy)-7-methoxy-quinazoline 4-[(3-chloro-4-fluoro-phenyl)amino]-6-(1-cyano-piperidin-4-yloxy)-7-methoxy-quinazoline optionally in the form of the racemates, enantiomers, diastereomers thereof and optionally in the form of the pharmacologically acceptable acid addition salts, solvates or hydrates thereof. According to the invention these acid addition salts are preferably selected from among the hydrochloride, hydrobromide, hydriodide, hydrosulphate, hydrophosphate, hydromethanesulphonate, hydronitrate, hydromaleate, hydroacetate, hydrocitrate, hydrofumarate, hydrotartrate, hydroxalate, hydrosuccinate, hydrobenzoate and hydro-p-toluenesulphonate.

The dopamine agonists used are preferably compounds selected from among bromocriptin, cabergoline, alpha-dihydroergocryptine, lisuride, pergolide, pramipexol, roxindol, ropinirol, talipexol, tergurid and viozan, optionally in the form of the racemates, enantiomers, diastereomers thereof and optionally in the form of the pharmacologically acceptable acid addition salts, solvates or hydrates thereof. According to the invention these acid addition salts are preferably selected from among the hydrochloride, hydrobromide, hydriodide, hydrosulphate, hydrophosphate, hydromethanesulphonate, hydronitrate, hydromaleate, hydroacetate, hydrocitrate, hydrofumarate, hydrotartrate, hydrooxalate, hydrosuccinate, hydrobenzoate and hydro-p-toluenesulphonate.

H1-Antihistamines which may be used are preferably compounds selected from among epinastine, cetirizine, azelastine, fexofenadine, levocabastine, loratadine, mizolastine, ketotifen, emedastine, dimetindene, clemastine, bamipine, cexchlorpheniramine, pheniramine, doxylamine, chlorophenoxamine, dimenhydrinate, diphenhydramine, promethazine, ebastine, desloratidine and meclozine, optionally in the form of the racemates, enantiomers, diastereomers thereof and optionally in the form of the pharmacologically acceptable acid addition salts, solvates or hydrates thereof. According to the invention these acid addition salts are preferably selected from among the hydrochloride, hydrobromide, hydriodide, hydrosulphate, hydrophosphate, hydromethanesulphonate, hydronitrate, hydromaleate, hydroacetate, hydrocitrate, hydrofumarate, hydrotartrate, hydroxalate, hydrosuccinate, hydrobenzoate and hydro-p-toluenesulphonate.

It is also possible to use inhalable macromolecules as disclosed in EP 1 003 478.

In addition, the compound may come from the group of ergot alkaloid derivatives, the triptans, the CGRP-inhibitors, the phosphodiesterase-V inhibitors, optionally in the form of the racemates, enantiomers or diastereomers thereof, optionally in the form of the pharmacologically acceptable acid addition salts, the solvates and/or hydrates thereof.

Examples of ergot alkaloid derivatives are dihydroergotamine and ergotamine.

For inhalation it is possible to use medicaments have the above-mentioned active substances, as well as the salts and esters thereof and combinations of these active substances, salts and esters.

Preferably, the chamber is arranged in a chamber receptacle of a plate that is pivotably jointed to the housing and capable of being latched to the housing. Accordingly, the chamber is first coupled to the chamber receptacle arranged on the plate and then the plate with the chamber receptacle is pivoted into a position of use in which the plate is latched to the housing and closes it off.

Preferably, means are provided which hold the chamber in a defined position. The means secure the chamber relative to a mouthpiece, for example. The means are expediently in the form of at least one tongue and groove connection. It is possible, for example, for the chamber receptacle to have a groove and for the chamber to have a corresponding tongue, or vice versa, the groove extending over the tongue when the chamber is placed in the chamber receptacle and in this way the two components are secured to one another. It is also possible to make the tongue and the groove conical in shape so that at a certain depth of penetration a clamping effect occurs. Preferably, the means comprise a push-in coding. This prevents the chamber from being inserted in the chamber receptacle in a skewed position. Advantageously, a stop for the pushed-in end position of the chamber is provided in the chamber receptacle.

According to a further feature, the chamber is substantially cylindrical in cross section, while the end face pointing in the direction of a mouthpiece is connected to an inhalation channel that leads to the mouthpiece and the end face opposite the mouthpiece is operatively connected to an air inlet opening of the housing. According to a further feature, the chamber is non-releasably attached to the inhalation channel and can be replaced together with the inhalation channel. The one-piece construction of the chamber with the inhalation channel may be achieved for example by manufacturing by injection moulding of plastics and ensures that essential components of the inhaler which come into contact with the medicament during inhalation are replaced.

Preferably the plastics are polymers, thermoplastic polycondensates, polyadducts, modified natural substances or rubbers or mixtures of these plastics.

Particularly preferred are polyolefins, vinyl chloride polymers, styrene polymers, polyacetals, polyamides, thermoplastic polyesters and polyarylethers or mixtures of these plastics. Examples of these plastics are polyethylene, polyvinyl chloride, polyoxymethylene, polyacetal, acrylonitrile/butadiene/styrene (ABS), acrylonitrile/styrene/acrylic ester (ASA), polyamides, polycarbonate, poly(ethyleneterephthalate), poly(butyleneterephthalate) or poly(phenylene ether). Plastics of this kind may be obtained for example from the company Ensinger in Nufringen, Germany.

Expediently, a component, particularly a screen, for dispersing particles is arranged in the inhalation channel. Accordingly, on inhalation, the medicament, which has been micronised, in particular, passes through the screen to the user of the inhaler.

In order to ensure an adequate flow of air through the chamber during inhalation and hence to guarantee that the medicament is expelled from the capsule and delivered by the current of air, the chamber has, on its end face opposite the inhalation channel, a connector for coupling to the air inlet opening of the housing. For removing the chamber from the chamber receptacle the connector usefully projects beyond the chamber receptacle. By applying pressure to the connector in the axial direction of the chamber it can be pressed out of the chamber receptacle and removed.

To allow easy opening of the capsule contained in the chamber which protects the medicament from environmental effects, the chamber has on its circumference two bores at a spacing from one another in which pins engage for piercing the capsule at its ends, the pins being movably mounted in the chamber receptacle and being capable of being acted upon by an actuating element. Obviously the scope of the invention also includes the provision of only one pin movably mounted in the chamber receptacle and capable of being operated by the actuating element to pierce the capsule.

Preferably, the chamber is designed for single use and contains the capsule. The capsule may be accommodated in the chamber at the time of manufacture in such as way that it cannot be lost or removed and is intended for a single inhalation. After inhalation the chamber together with the emptied capsule is removed from the inhaler and discarded. As a result, there is a clean chamber available for every inhalation, optionally with an associated inhalation channel and connector.

For visual checking to see whether a capsule has been placed in the chamber or whether all the medicament provided has been inhaled, the chamber is made of a transparent plastics. Preferably, the housing and the chamber receptacle have at least one area made of transparent plastics, in particular a window, at least in the region of the chamber.

In order to produce an inhaler which is of compact design and easy to carry, the mouthpiece and a lid are advantageously pivotably mounted on the housing together with the plate, while the mouthpiece can be latched to the plate and the lid can be latched to the housing.

It will be understood that the features mentioned above and still to be described hereinafter may be used not only in the particular combination mentioned but also in other combinations. The scope of the invention is defined only by the claims.

The invention is hereinafter described in more detail by means of an exemplifying embodiment with reference to the associated drawings, wherein.

Figure 1:
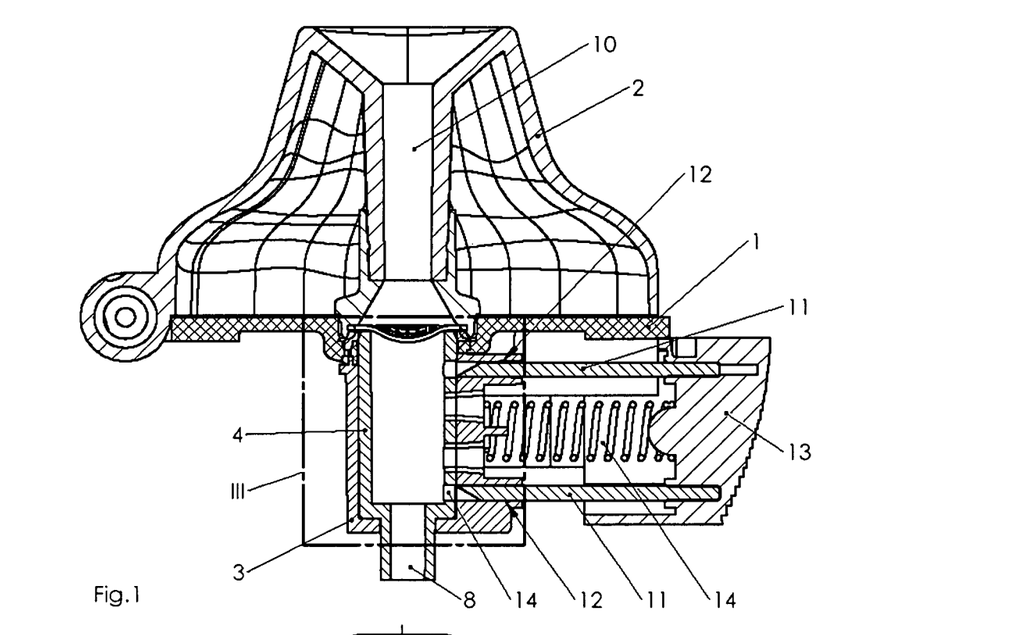
FIG. 1 is a partial view of an inhaler according to the invention.
Figure 2:
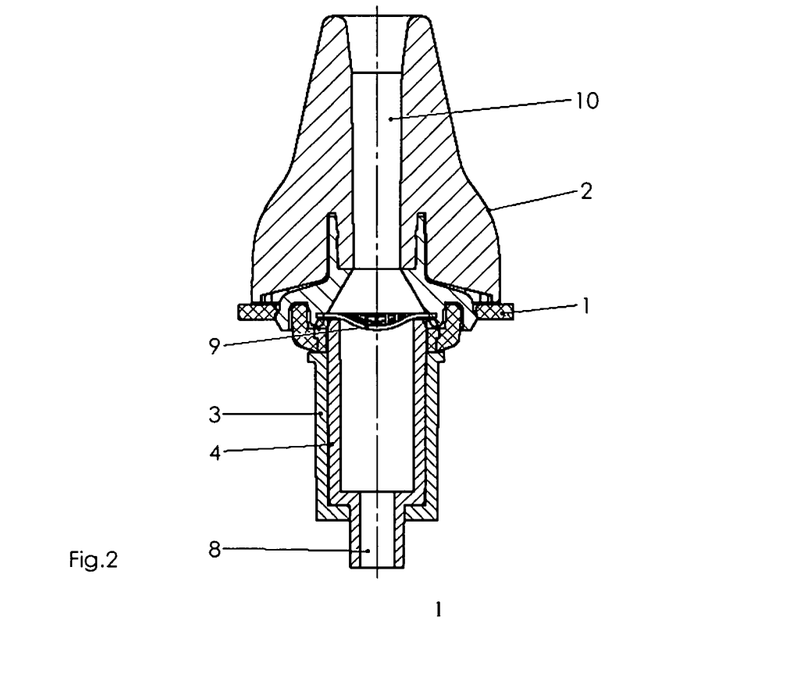
FIG. 2 is another partial view of the inhaler according to FIG. 1.
Figure 3:
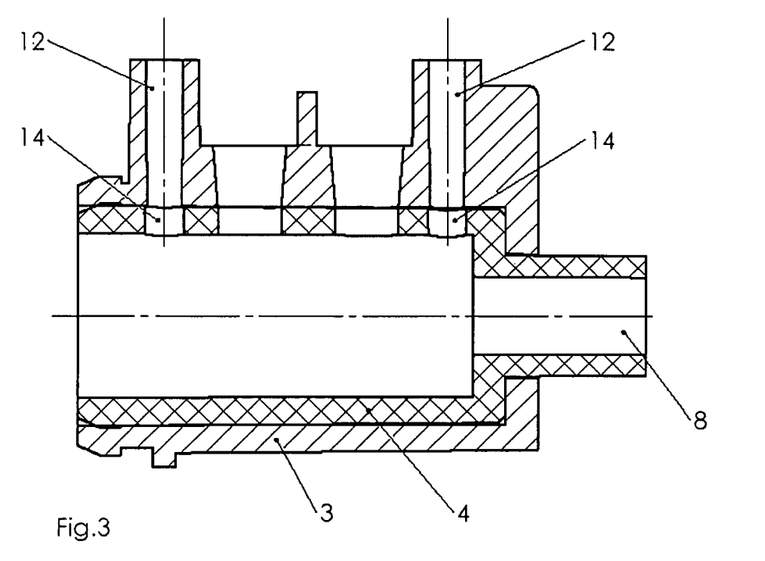
FIG. 3 is a magnified view of the detail III from FIG. 1.
Figure 4:
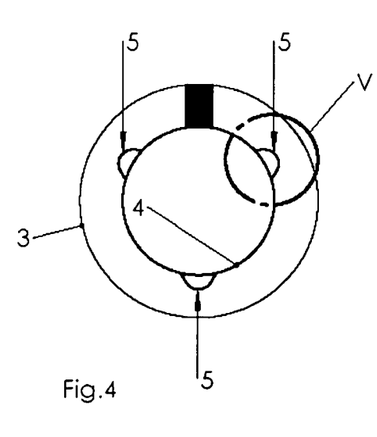
FIG. 4 is a schematic view of a cross-section through the detail in FIG. 3.
Figure 5:
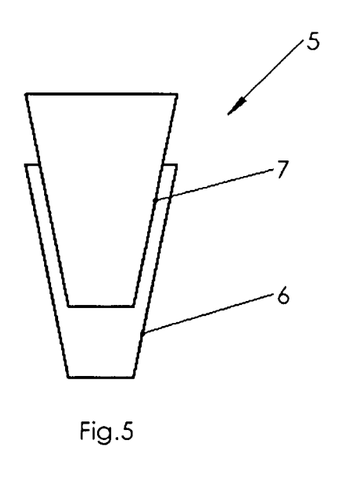
FIG. 5 is a magnified side view of the detail V from FIG. 4.

The inhaler comprises a housing formed as a lower part to which a plate 1 is pivotably jointed, which closes off the housing in a latched end position. Together with the plate 1, a mouthpiece 1 and a lid are mounted on the housing, the mouthpiece 2 together with the plate 1 and the lid being adapted to be latched to the housing. On the plate 1 is provided a chamber receptacle 3 which is designed for replaceably inserting a chamber 4 to accommodate a capsule containing a medicament. The chamber receptacle 3 is fixed to the plate 2 such that it can be pivoted into the housing and out of the housing. In order to hold the chamber 4 in a defined position relative to the chamber receptacle 3, an insertion coding is provided in the form of three tongue and groove connections 5 unevenly distributed about the circumference, which also ensure that the chamber 4 can only be inserted in the chamber receptacle 3 in a specific position. The grooves 6 and the tongues 7 engaging therein are of conical form such that they taper starting from the plate in order to allow the chamber 4 to be attached to the chamber receptacle 3 in a comparatively simple manner, on the one hand, and to achieve a clamping action at least in an end position of the chamber 3 in which it has been pushed into the chamber receptacle 3, on the other hand.

The chamber 4 has a connector 8, through which air enters the chamber 4 during inhalation and which projects beyond the free end of the chamber receptacle 3 on the side remote from the mouthpiece 2. When the user applies manual pressure to the connector 8 the chamber 4 is pressed out of the chamber receptacle 3 to enable it to be changed. On the side facing the mouthpiece 2, the chamber 3 abuts on a screen 9 which is inserted in an inhalation channel 10 in order to disperse particles.

For piercing the capsule immediately before inhalation, two pins 11 at a spacing from one another are mounted to be movable in guide connectors 12 of the chamber receptacle 3, each being associated with a common actuating element 13. The guide connectors 12 of the chamber receptacle 3 correspond to bores 14 on the circumference of the chamber 4 through which the pins 11 pass into the interior of the chamber 4 and thus enter the capsule. After the capsule has been pierced by means of the pins 11, the pins 11 are reset by a compression spring 14 arranged between the chamber receptacle 4 and the actuating element 13 in order to expose the holes in the capsule.

The invention claimed is:

1. An inhaler for administering a medicament in the form of inhalable substances, formulations or mixtures of substances, comprising:
   a housing;
   a chamber receptacle disposed within the housing and including a cylindrical internal volume having respective first and second openings at opposite ends thereof; and
   a single-use chamber having: (i) a substantially cylindrical body sized and shaped to be releasably received into the first end of the chamber receptacle, and (ii) a single-use capsule containing the medicament disposed within the body in such a way that it cannot be lost or removed,
   wherein the single-use chamber is removable through the first opening of the chamber receptacle so as to empty the cylindrical internal volume of the chamber receptacle and permit the loading on a further single-use chamber therein.

2. The inhaler according to claim 1, further comprising:
   a plate pivotably joined to the housing and including an opening therethrough,
   wherein the chamber receptacle is capable of being latched to the plate such that the first opening of the chamber receptacle is in communication with the opening through the plate.

3. The inhaler according to claim 1, further comprising means for holding the chamber in a defined position.

4. The inhaler according to claim 3, wherein the means are in the form of at least one tongue and groove connection.

5. The inhaler according to claim 3, wherein the chamber receptacle and the single-use chamber define a longitudinal axis, and the means comprise an insertion coding that ensures the single-use chamber is inserted into the chamber receptacle in one specific rotational position about the longitudinal axis.

6. The inhaler according to one of claim 1, wherein the chamber receptacle forms a stop for the chamber at a pushed-in end position.

7. The inhaler according to claim 1, further comprising:
   a mouthpiece;
   an inhalation channel in communication with the mouthpiece;
   the single-use chamber is substantially cylindrical in cross-section having an end face pointing toward the mouthpiece that is connected to the inhalation channel, and having an end face opposite the mouthpiece that is operatively connected to an air inlet opening in the housing.

8. The inhaler according to claim 7, wherein the single-use chamber is non-releasably connected to the inhalation channel and the single-sue chamber is replaced together with the inhalation channel.

9. The inhaler according to claim 7, further comprising a component for dispersing particles disposed in the inhalation channel.

10. The inhaler according to claim 7, wherein: the single-use chamber comprises, on the end face opposite the inhalation channel, a connector for coupling to the air inlet opening of the housing, and the connector projects beyond a free end of the chamber receptacle on a side remote from the mouthpiece.

11. The inhaler according to claim 1, wherein the single-use chamber comprises, on its circumference, two spaced-apart bores in which pins for piercing the ends of the capsule engage, the pins being movably mounted in the chamber receptacle and being capable of being operated by an actuating element.

12. The inhaler according to claim 1, wherein the single-use chamber is made from a transparent plastics and the housing and the chamber receptacle comprise, at least in a region of the single-use chamber, at least one region made of a transparent plastics material.

13. The inhaler according to claim 1, further comprising:
a lid;
wherein the plate, the mouthpiece, and the lid are pivotably joined to the housing, the mouthpiece is capable of being latched to the plate, and the lid is capable of being latched to the housing.

14. The inhaler according to claim 1, wherein the chamber receptacle, the single-use chamber, and the single-use capsule cooperate for administering the medicament, and the medicament is a powdered medicament.

15. The inhaler according to claim 14, wherein the powdered medicament is selected from among the anticholinergics, betamimetics, steroids, phosphodiesterase-IV-inhibitors, LTD4-antagonists, EGFR-kinase inhibitors, antiallergics, ergot alkaloid derivatives, triptans, CGRP antagonists, phosphodiesterase-V-inhibitors, and combinations of such active substances.

16. The inhaler according to claim 1, wherein the medicament is a powdered medicament.

17. The inhaler according to claim 1, further comprising:
two guide connectors disposed within the chamber receptacle;
a respective pin movably mounted in each of the guide connectors; and
two bores through the single-use chamber,
wherein the two bores and the two guide connectors are disposed in such way that the two pins pass into the single-use chamber and pierce the capsule.

* * * * *